United States Patent [19]
Kinouchi et al.

[11] Patent Number: 5,337,033
[45] Date of Patent: Aug. 9, 1994

[54] PERMANENT MAGNET ASSEMBLY FOR STABLY FIXING DENTURE

[75] Inventors: Yohsuke Kinouchi, Tokushima; Minoru Ai, Tokyo; Hiroshi Mizutani, Hino; Osamu Okuno, Tokyo; Kiyotaka Yamauchi, Kumagaya; Akira Yamataka, Saitama; Hiroya Suzuki, Kumagaya, all of Japan

[73] Assignee: Hitachi Metals, Ltd., Tokyo, Japan

[21] Appl. No.: 820,415

[22] Filed: Jan. 15, 1992

[30] Foreign Application Priority Data

Jun. 13, 1991 [JP] Japan ................................. 3-141691

[51] Int. Cl.$^5$ ....................... H01F 7/02; A61C 13/235
[52] U.S. Cl. ....................................... 335/302; 433/189
[58] Field of Search ............................... 335/302, 304; 219/121.63, 121.64; 433/189

[56] References Cited

U.S. PATENT DOCUMENTS

| | | | |
|---|---|---|---|
| 4,530,663 | 7/1985 | Portnoy | 433/189 |
| 4,815,975 | 3/1989 | Garrel et al. | 433/189 |
| 5,013,243 | 5/1991 | Tanaka et al. | 433/189 |

OTHER PUBLICATIONS

"The Application of Rare Earth Magnetic Retention to Osseointegrated Implants," Thomas R. Jackson, The International Journal of Oral and Maxillofacial Implants, vol. 1, No. 2, 1986.

*Primary Examiner*—Harold Broome
*Attorney, Agent, or Firm*—Finnegan, Henderson, Farabow, Garrett & Dunner

[57] ABSTRACT

A permanent magnet assembly for stably fixing a denture comprising a permanent magnet, a casing made of a corrosion-resistant, magnetic material having a cavity for receiving the permanent magnet, and a seal plate for covering an opening of the casing to prevent the permanent magnet from exposing outside, the seal plate consisting of a seal ring member made of a corrosion-resistant, non-magnetic material and a disc plate made of a corrosion-resistant, soft-magnetic material and having substantially the same outer diameter as the inner diameter of the seal ring member, the seal ring member and the disc plate being concentrically arranged in the same plane, the disc plate being welded to the seal ring member in their abutment, and the seal ring member being welded to the casing. Laser welding is utilized.

7 Claims, 6 Drawing Sheets

PERMANENT MAGNET ASSEMBLY FOR STABLY FIXING DENTURE

BACKGROUND OF THE INVENTION

The present invention relates to a permanent magnet assembly for stably fixing a denture by utilizing a magnetic attraction force of a permanent magnet.

Various attempts have already been made to fix a denture by utilizing an attraction force of a permanent magnet to a soft-magnetic alloy. One example of such attempts is described in "Application of Rare Earth Magnets to Osseo-Integrated Implant," T. R. Jackson, Oral Maxillofacial Implant, Vol. 1, No. 2 (1987), pp. 77-89.

To practically use such a denture, it is necessary that a permanent magnet is completely sealed in a member made of a material whose harmlessness to human body is fully verified, and that there is little magnetic flux leaking outside from the permanent magnet member. For instance, a permanent magnet assembly having a constitution as shown in FIG. 9 has been used. In FIG. 9, (a) is a schematic perspective view showing the permanent magnet assembly, and (b) is a schematic view showing the cross section of the permanent magnet assembly. A cylindrical rare earth-cobalt magnet 1 axially magnetized as shown by the arrow is received in a cylindrical casing 2 made of a magnetic stainless steel alloy having excellent corrosion resistance, and covered by a thin disc plate 3 made of a non-magnetic stainless steel alloy having excellent corrosion resistance, these members being bonded to each other by an adhesive 4 to seal the inside of the casing 2.

Such a permanent magnet assembly constituted by the permanent magnet 1, the casing 2 and the disc plate 3 is buried in a denture plate 8 for fixing the denture as shown in FIG. 10. Buried in an alveolus 9 is a root member 7 made of a soft-magnetic alloy as shown in FIG. 10. When the magnet assembly is placed on the root member 7 with the non-magnetic disc plate 3 of the magnet assembly facing the root member 7, a magnetic attraction force is generated between the magnet assembly and the root member 7. By this attraction force, the denture plate 8 is fixed to the alveolus 9. At this time, the magnetic flux generated from the magnet 1 flows through a circular course from the magnet 1 to the root member 7, the casing 2 and then to the magnet 1. Accordingly, there is extremely little magnetic flux leaking outside from the permanent magnet assembly. Also, since the casing 2 and the disc plate 3 are made of stainless steel materials, they are corrosion-resistant and show practically sufficient wear resistance when they are used for fixing the denture and subjected to dental articulation. With respect to the adhesive 4, it has been considered to be sufficient in sealability and chemical stability when used in the mouth.

However, the inventors have found that the permanent magnet assembly having the above structure is disadvantageous in that since the adhesive 4 is made of an organic material it is still insufficient in adhesion strength and chemical stability for a long period of use despite its practically sufficient properties. Also, despite the fact that the conventional permanent magnet assembly of FIG. 9 is excellent in preventing the leakage of magnetic flux, it fails to provide a sufficient attraction force. Accordingly, a more reliable permanent magnet assembly of a seal type capable of fixing the denture stably with a larger attraction force is desired.

OBJECT AND SUMMARY OF THE INVENTION

Accordingly, an object of the present invention is to provide a more reliable permanent magnet assembly for stably fixing the denture with a larger attraction force.

As a result of intense research in view of the above object, the inventors have found that by welding a seal plate to a casing, it is possible to prevent an adhesive for bonding a permanent magnet to the casing from exposing outside, and that by constituting the seal plate by a non-magnetic seal ring member and a magnetic disc plate concentrically arranged, and by welding them to the casing, a higher magnetic attraction force can be obtained without exposing the adhesive.

Thus, the first permanent magnet assembly for stably fixing a denture according to the present invention comprises a permanent magnet, a casing made of a corrosion-resistant, magnetic material having a cavity for receiving the permanent magnet, and a seal plate made of a corrosion-resistant, non-magnetic material for covering an opening of the casing to prevent the permanent magnet from exposing outside, each of the members being welding to each other in their abutment.

The second permanent magnet assembly for stably fixing a denture according to the present invention comprises a permanent magnet, a casing made of a corrosion-resistant, magnetic material having a cavity for receiving the permanent magnet, and a seal plate for covering an opening of the casing to prevent the permanent magnet from exposing outside, the seal plate consisting of a seal ring member made of a corrosion-resistant, non-magnetic material and a disc plate made of a corrosion-resistant, soft-magnetic material and having substantially the same outer diameter as the inner diameter of the seal ring member, the seal ring member and the disc plate being concentrically arranged in the same plane, the disc plate being welding to the seal ring member in their abutment, and the seal ring member being welding to the casing.

DETAILED DESCRIPTION OF THE INVENTION

Figure 1A:
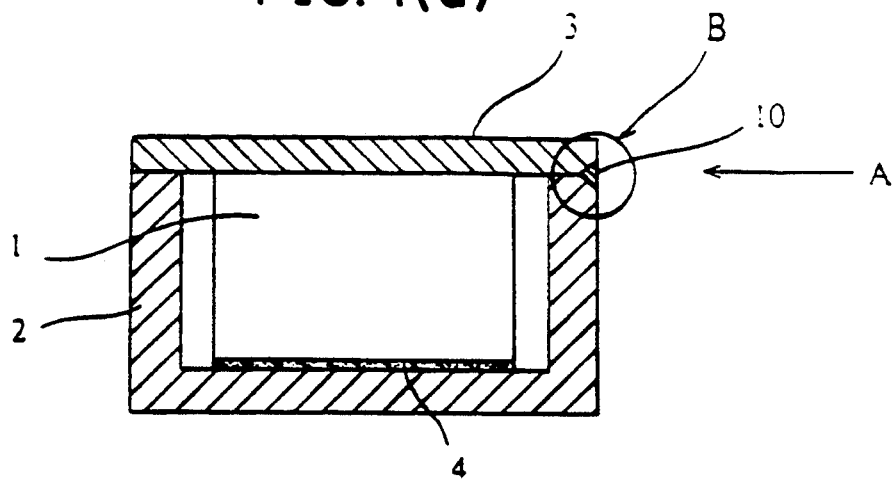
FIG. 1(a) is a schematic cross-sectional view showing a permanent magnet assembly according to one embodiment of the present invention.

The present invention will be explained in detail below.

In the present invention, the seal plate may be a single member made of a non-magnetic material, but it is preferable that the seal plate is constituted by a seal ring member made of a corrosion-resistant, non-magnetic material and a disc plate having substantially the same outer periphery as an inner periphery of the seal ring member and made of a corrosion-resistant, soft-magnetic material. In this case, since the disc plate is made of a soft-magnetic material, there is only an extremely small magnetic gap between the permanent magnet and the root member, whereby the permanent magnet assembly can exert a drastically improved attraction force to the root member.

Also, in the permanent magnet assembly of the present invention, the casing is sealed not by an adhesive but preferably by welding, it shows extremely improved reliability in chemical stability, adhesion strength, etc. The sealing means with a metal material is generally welding, soldering, brazing, etc. However, from the aspect of achieving complete sealing and harmlessness to human body, it is necessary to utilize welding, which can avoid the deterioration of a metal material and can provide an extremely small sealed portion. Incidentally, only metals whose safety to human body is fully confirmed should be used in the present invention.

Since the permanent magnet used in the present invention should have as strong magnetic flux as possible with a small size, Sm-Co magnets or Nd-Fe-B magnets are used, Also, the shape of the permanent magnet is usually cylindrical, although it may vary depending on a position thereof in the permanent magnet assembly. Accordingly, a ring-shaped thin plate is usually used as a seal ring member, and a disc-shaped thin plate is usually used as a center seal plate. The permanent magnet is usually magnetized before placed in the casing, although it may be magnetized after assembling.

The present invention will be explained in further detail by way of the specific examples below.

FIG. 1 shows one example of the permanent magnet assembly of the present invention. A cylindrical permanent magnet having an outer diameter of 2 mm and a height of 1.5 mm is fixed by an adhesive 4 to the bottom of a cavity of a cylindrical casing 2 having an outer diameter of 3 mm, an inner diameter of 2.4 mm and a height of 2 mm. Disposed on the casing 2 is a seal plate 3 having substantially the same outer diameter as that of the casing 2, and the seal plate 3 is welded to the casing 2. The arrow A shows a direction of a laser beam for welding, and 10 denotes a welded portion. Incidentally, the cylindrical casing 2 is made of a corrosion-resistant, magnetic material, and the seal plate 3 is made of a corrosion-resistant, non-magnetic material.

Since the adhesive 4 is not exposed outside in the permanent magnet assembly of such a structure, the deterioration of the adhesive 4 with time can be completely prevented, resulting in a highly reliable permanent magnet assembly.

Figure 1B:
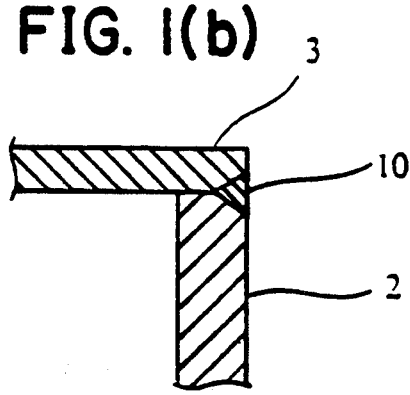
FIG. 1(b) is an enlarged view of a portion of the permanent magnet assembly of FIG. 1(a), which is indicated by a circle B.
Figure 1C:
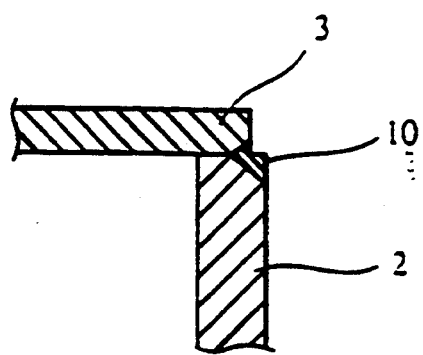
FIG. 1(c) is an enlarged view of one undesirable example of the portion B of the permanent magnet assembly of FIG. 1(a)
Figure 1D:
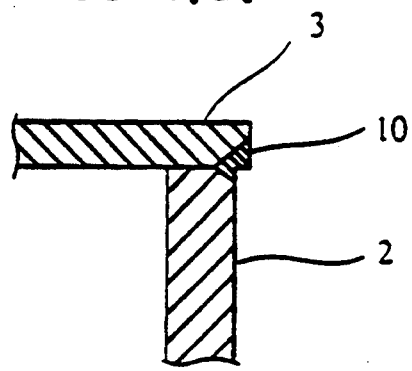
FIG. 1(d) is an enlarged view of another undesirable example of the portion B of the permanent magnet assembly of FIG. 1(a)

Incidentally, in this structure, there is a problem that it is rather difficult to precisely position the the seal plate 3 to the casing 2 in such a manner that a periphery of the seal plate 3 is completely aligned with a cylindrical side surface of the casing 2. Therefore, it is difficult to achieve the reliable welding without fail. More specifically, to achieve the precise welding, the casing 2 and the seal plate 3 should be aligned in the welded portion 10 as shown in FIG. 1(b). Although the diameter of the laser beam can be reduced to an order of as small as about 10 $\mu$m, the welding is extremely non-uniform and defective, if both members are not completely aligned as shown in FIG. 1(c) and (d) depicting a portion B in FIG. 1(a). Nevertheless, it is not easy to achieve the complete alignment of the seal plate 3 to the casing 2, due to the working tolerance and the positioning precision of the two members. Also, since the welding is conducted on a circular side surface of the cylindrical member, the cylindrical member is rotated while welding. Accordingly, the precise setting of the assembled cylindrical member consisting of the casing 2 and the seal plate 3 is not necessary.

Further, to keep the attraction force of the permanent magnet at a high level, the seal plate 3 should be as thin as possible, for instance, about 15 $\mu$m. Therefore, the precision of the laser beam irradiation should be sufficiently high. In addition, the seal plate 3 will have a small heat capacity, resulting in a large discrepancy in a heat capacity between the seal plate 3 and the casing 2. Thus, it is likely that the seal plate 3 is evaporated in the course of the welding, failing to achieve the reliable welding.

Figure 2:
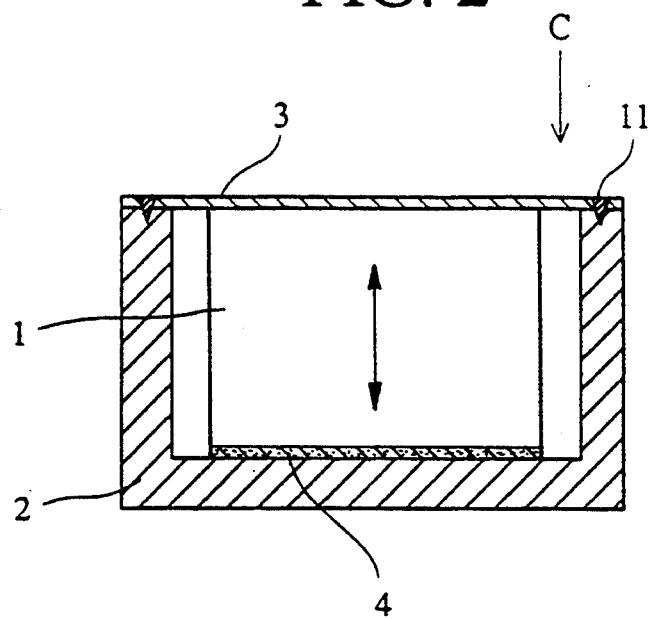
FIG. 2 is a schematic cross-sectional view showing a permanent magnet assembly according to another embodiment of the present invention.

To avoid such problems, the inventors have considered a permanent magnet assembly having a structure as shown in FIG. 2. In FIG. 2, a laser beam is irradiated in the direction C to achieve welding. However, if the seal plate 3 is thin, it is likely to be evaporated in the course of welding, failing to provide a sufficient improvement.

Figure 9A:
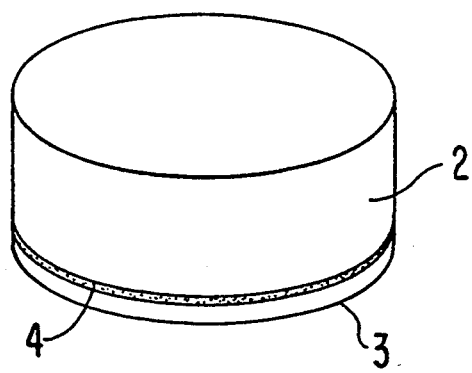
FIG. 9(a) is a schematic perspective view showing a conventional permanent magnet assembly.
Figure 9B:
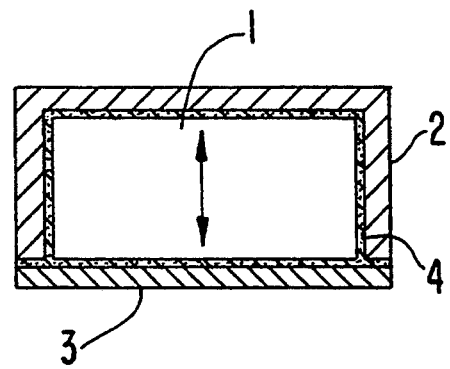
FIG. 9(b) is a schematic cross-sectional view showing the conventional permanent magnet assembly of FIG. 9(a)

In addition, although a magnetic gap decreases in the permanent magnet assembly of the above structure by the thickness of the adhesive as compared with the conventional permanent magnet assembly of FIG. 9, improvement is not necessarily sufficient, because there is a non-magnetic seal plate 3 between the permanent magnet 1 and the root member.

Figure 3:
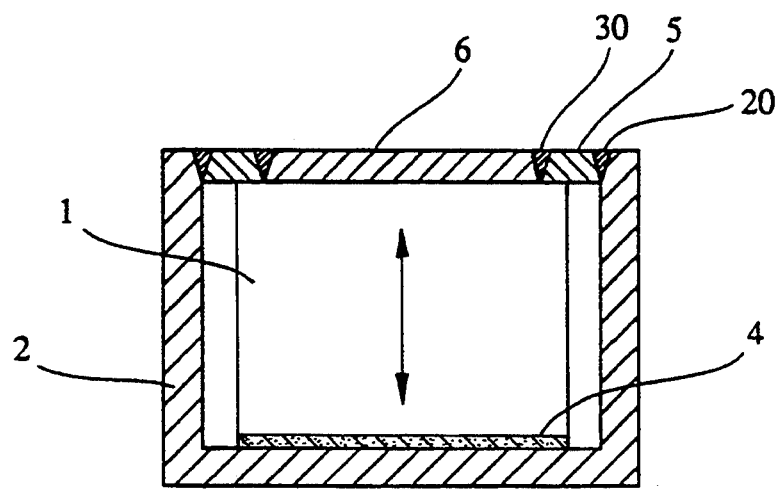
FIG. 3 is a schematic cross-sectional view showing a permanent magnet assembly according to a further embodiment of the present invention.

FIG. 3 shows a permanent magnet assembly according to a further embodiment of the present invention. In FIG. 3, 1 denotes a permanent magnet, 2 denotes a corrosion-resistant, magnetic stainless steel casing, 4 denotes an adhesive, 5 denotes a seal ring member made of corrosion-resistant, non-magnetic stainless steel, and 6 denotes a disc-shaped seal plate (simply "disc plate") made of corrosion-resistant, magnetic stainless steel. The seal ring member 5 and the disc plate 6 constitute a seal plate.

This permanent magnet assembly has been devised to avoid the problems that arise in the case of welding of the permanent magnet assembly of FIG. 1. The direction of the laser beam irradiation is perpendicular not to the cylindrical side surface of the casing 2 but to the seal plate. Further, the laser beam is focused to provide irradiation to an interface of the abutted members.

More importantly, it should be noted that to increase the attraction force, the seal plate is constituted by the disc plate 6 made of magnetic stainless steel and the seal ring member 5 made of non-magnetic stainless steel, arranged such that the disc plate 6 is positioned inside the seal ring member 5 in the same plane. Also, the seal plate consisting of the disc plate 6 and the seal ring member 5 is extremely thicker than the seal plate of the permanent magnet assembly in FIG. 1, for instance, about 250 $\mu$m. Therefore, the magnetic flux generated from the permanent magnet 1 magnetized in the direction as shown by the arrow can easily reach the surface of the disc plate 6 made of magnetic stainless steel.

Figure 10:
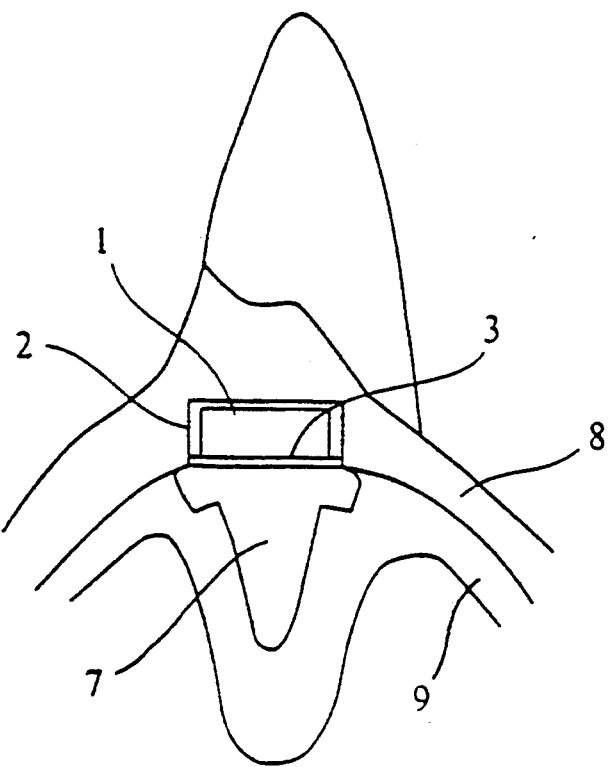
FIG. 10 is a schematic cross-sectional view showing the conventional permanent magnet assembly embedded in a denture plate for fixing the denture.

Accordingly, when the permanent magnet assembly of this embodiment is placed at such a position as to face the root member 7 as shown in FIG. 10, the permanent magnet assembly can show a magnetic attraction force about 7% higher than the conventional permanent magnet assembly shown in FIG. 9. Also, since the seal ring member 5 is made of a non-magnetic material in this embodiment, a magnetic short circuiting between an outer side portion of the casing 2 and the disc plate 6 can be prevented.

Incidentally, in this embodiment, the width of the seal ring member 5 is, for instance, 0.4 mm, but it may be changed properly in order to prevent the above magnetic short circuiting and to avoid the melted portions 20, 30 from being brought into contact with each other.

Figure 4:
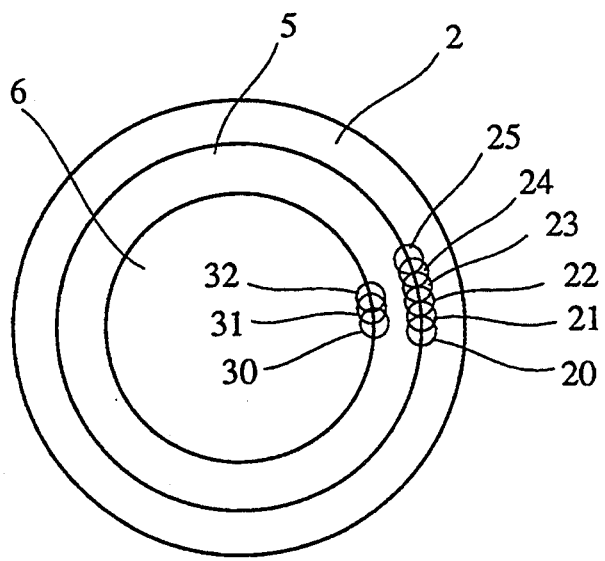
FIG. 4 is a plan view showing the permanent magnet assembly of FIG. 3.

FIG. 4 is a plan view of the permanent magnet assembly of FIG. 3. In FIG. 4, 20–25 and 30–32 denote spots of laser beam welding. Specifically, by use of an irradiating laser beam having a properly reduced diameter, a portion 20 is melted in a conical shape, leading to the complete bonding of the seal ring member 5 to the casing 2. Next, the irradiation spot of the laser beam is moved precisely to a portion 21 by a proper means such as numerical control. Similarly, by sequential use of the irradiating laser beam, a portion 21 is melted in a conical shape, leading to the complete bonding of the seal ring member 5 to the casing 2. Since the melted portions 20 and 21 partially overlap each other, there is no unwelded portion between the adjacent laser beam spots. Thus, by continuing the laser beam welding in portions 22, 23. . . , the seal ring member 5 is finally completely welded to the casing 2. Incidentally, FIG. 4 shows only laser beam spots 20–25, but it should be noted that such laser beam spots exist along the entire length of the circular interface between the seal ring member 5 and the casing 2.

With respect to the abutted portions of the seal ring member 5 and the disc plate 6, the same laser beam welding is conducted in laser beam spots 30, 31, 32. . . , to achieve the completely welding of the disc plate 6 to the seal ring member 5.

Thus, the inside of the casing 2 is completely sealed by the seal plate consisting of the seal ring member 6 and the disc plate 5 welded to the casing 2. The outside of the permanent magnet assembly is made of stainless steel materials which have excellent corrosion resistance and wear resistance, and are harmless to human body, and its welded portions are also safe.

Although it is likely that there are gaps in the abutment of the seal ring member 5 to the casing 2 and in the abutment of the disc plate 6 to the seal ring member 5 due to the working and setting tolerance of these members, the gap can be filled by a metal by laser beam irradiation by properly controlling the diameter of the laser beam spot and the energy of the laser beam. For instance, in a case where there is a gap of about 0.07 mm, the laser beam spot having a diameter of 0.25–0.35 mm can cause the metal to fill the gap completely.

Figure 5:
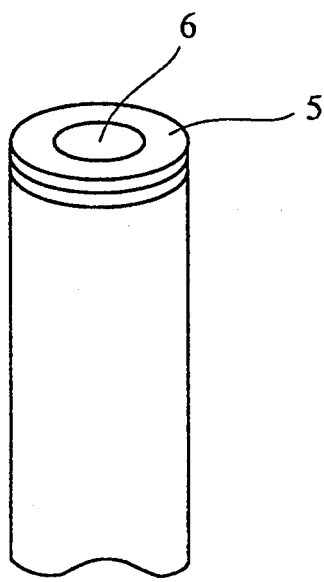
FIG. 5 is a perspective view showing the process of producing a seal plate used in the permanent magnet assembly of FIG. 3.

With respect to the seal ring member 5 and the disc plate 6, they can be produced by first preparing by extrusion an assembly consisting of a round rod for the disc plate 6 and a round pipe for the seal ring plate 5 concentrically covering the round rod, and slicing the assembly as shown in FIG. 5. By this method, it is possible to produce the seal ring member 5 and the disc plate 6 with no gap therebetween. Also, by adjusting the outer diameter of the seal ring member 6 and the inner diameter of the casing 2 such that the seal ring member 6 is fitted into the casing 2 by compression, the gap can be avoided between the seal ring member 6 and the casing 2.

In this embodiment, since the disc plate 6 is made of a magnetic stainless steel material, the magnetic attraction force can be enhanced. Also, since the magnetic attraction force is not reduced by increasing the thickness of the seal ring member 6 and the disc plate 6, the assembling and welding of the seal ring member 5 and the disc plate 6 to the casing 2 are much easier than in the case of the permanent magnet assembly of FIG. 1. In addition, the permanent magnet assembly of this embodiment can have a larger tolerance of wear during the period of use.

Incidentally, the corrosion-resistant, magnetic stainless steel used for the casing 2 and the disc plate 6 may be ferritic stainless steel having an extremely small carbon content, which contains 2 weight % of Mo, and 30 weight % of Cr. The corrosion-resistant, non-magnetic stainless steel used for the seal ring member 5 may be austenite stainless steel such as SUS 316L, etc. The laser beam welding is conducted in a nitrogen atmosphere. As a result of a corrosion test, it has been confirmed that the permanent magnet assembly keeps sufficient sealing.

Figure 6A:
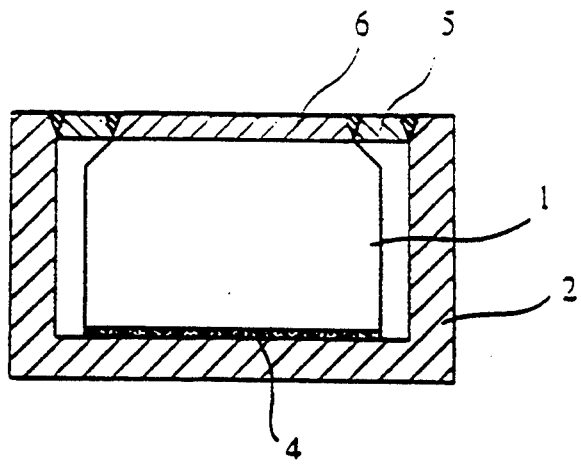
FIG. 6(a) is a schematic cross-sectional view showing a permanent magnet assembly according to a still further embodiment of the present invention.
Figure 6B:
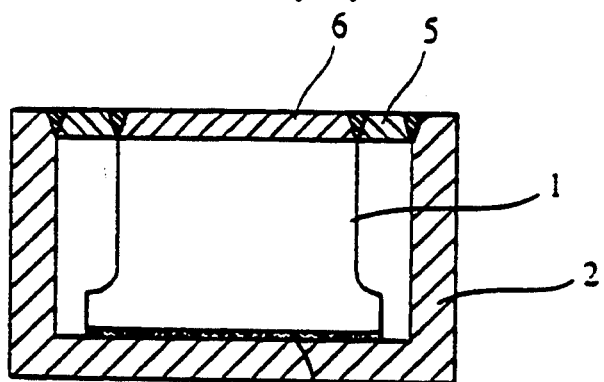
FIG. 6(b) is a schematic cross-sectional view showing a permanent magnet assembly according to a still further embodiment of the present invention.
Figure 6C:
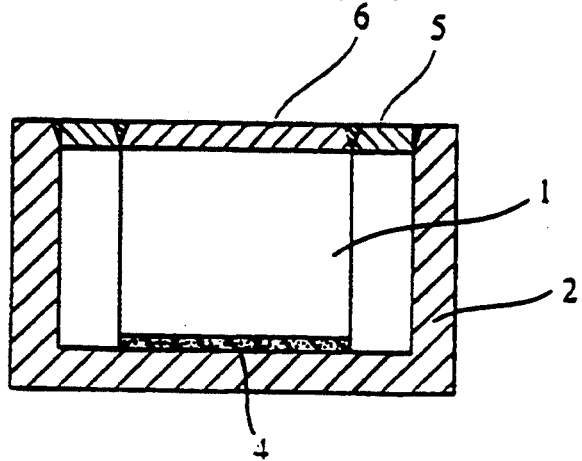
FIG. 6(c) is a schematic cross-sectional view showing a permanent magnet assembly according to a still further embodiment of the present invention.

FIGS. 6(a) to (c) show permanent magnet assemblies according to still further embodiments of the present invention. In any permanent magnet assembly, the permanent magnet 1 is placed inside the casing 2, as in the cases of the previous embodiments. However, in the present embodiment, the disc plate 6 is adjusted to have a diameter which is substantially the same as that of an upper surface of the permanent magnet 1, in order to efficiently gather the magnetic flux of the permanent magnet 1 to the disc plate 6, and to separate the disc plate 6 from the side surface of the casing 2.

Figure 7:
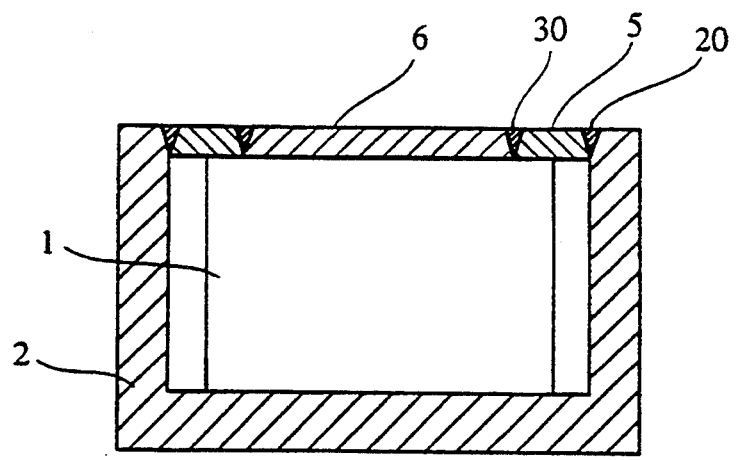
FIG. 7 is a schematic cross-sectional view showing a permanent magnet assembly according to a still further embodiment of the present invention.

FIG. 7 shows a permanent magnet assembly according to a still further embodiment of the present invention. For instance, a cylindrical permanent magnet 1 having an outer diameter of 3.2 mm and a height of 1.4 mm is placed in a casing 2 having an outer diameter of 4.4 mm, an inner diameter of 3.4 mm and a height of 2.1 mm. Disposed on the casing 2 is a seal plate consisting of a seal ring member 5 having an outer diameter of 3.4 mm and an inner diameter of 2.6 mm and a disc plate 6 having an outer diameter of 2.6 mm and a thickness of 0.25 mm.

In this embodiment, after placing the permanent magnet 1 inside the casing 2, the seal ring member 5 and the disc plate 6 are placed thereon, and the seal ring member 5 and the disc plate 6 are seam-welded to the casing 2 while they are pressed onto the casing 2 under pressure of about 1 kg/mm². Therefore, the permanent magnet 1 is fixed in the casing 2 without using an adhesive at all. Thus, the permanent magnet assembly of this embodiment is highly reliable due to the fact that an adhesive is not used for fixing the permanent magnet 1 to the casing 2. Also, by setting the outer diameter of the disc plate 6 and the inner diameter of the seal ring member 6 smaller than the outer diameter of the permanent magnet 1, both of the disc plate 6 and the seal ring member 5 are supported by an upper surface of the permanent magnet 1, making their seal welding easier.

Figure 8:
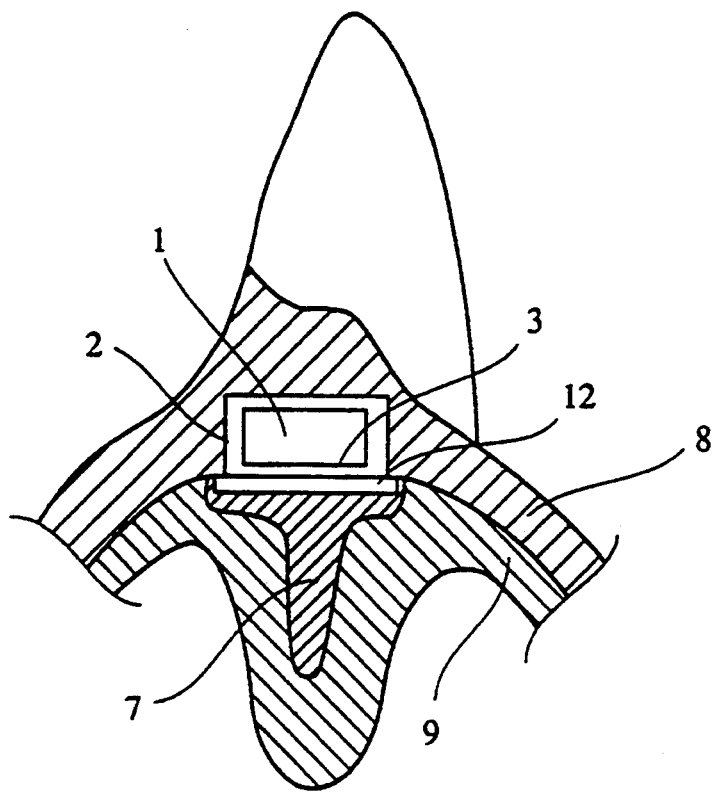
FIG. 8 is schematic cross-sectional view showing the permanent magnet assembly of the present invention embedded in a denture plate for fixing the denture.

FIG. 8 shows the denture using the permanent magnet assembly of the present invention, which is placed in the mouth, as in the case of FIG. 10. In the case of the present invention, since there is substantially no magnetic gap between the permanent magnet assembly and the root member, an excellent attraction force can be obtained. Also, in FIG. 8, a further improvement of the attraction force can be achieved by embedding in the root member 7 a plate 12 having a higher permeability than that of the root member 7.

As mentioned above, since the permanent magnet assembly for stably fixing the denture according to the present invention is completely sealed without an adhesive exposing outside, it is highly reliable and safe. Also, since a magnetic gap between the permanent magnet and the root member is extremely small, a high magnetic attraction force can be ensured, and a large tolerance of wear can be obtained.

What is claimed is:

1. A permanent magnet assembly for stably fixing a denture comprising:
   (a) a casing made of a corrosion-resistant, magnetic material having a cavity
   (b) a permanent magnet in said cavity of said casing, said permanent magnet being magnetized along a depth direction of said cavity of said casing; and
   (c) a seal plate for covering an opening of said casing to prevent said permanent magnet from being exposed to the outside, said seal plate consisting of a seal ring member made of a corrosion-resistant, non-magnetic material and a disc plate made of a corrosion-resistant, soft-magnetic material and having substantially the same outer diameter as the inner diameter of said seal ring member, said seal ring member and said disc plate being concentrically arranged in the same plane, said disc plate being welded to said seal ring member in their abutment, and said seal ring member being welded to said casing.

2. The permanent magnet assembly according to claim 1, wherein said seal plate is press-fitted into said casing before being welded to said casing.

3. The permanent magnet assembly according to claim 1, wherein said disc plate has an outer diameter smaller than an outer diameter of said permanent magnet.

4. The permanent magnet assembly according to claim 2, wherein said disc plate has an outer diameter smaller than an outer diameter of said permanent magnet.

5. The permanent magnet assembly according to claim 1, wherein said permanent magnet is in a shape of a disc or a solid or hollow cylinder, said permanent magnet being magnetized axially.

6. The permanent magnet assembly according to claim 2, wherein said permanent magnet is in a shape of a disc or a solid or hollow cylinder, said permanent magnet being magnetized axially.

7. The permanent magnet assembly according to claim 1, wherein respectively laser-welds join said disc plate to said seal ring member and said seal ring member to said casing.

* * * * *